(12) United States Patent
Mermoud et al.

(10) Patent No.: US 10,220,167 B2
(45) Date of Patent: Mar. 5, 2019

(54) MECHANISMS TO PREVENT ANOMALY DETECTORS FROM LEARNING ANOMALOUS PATTERNS

(71) Applicant: Cisco Technology, Inc., San Jose, CA (US)

(72) Inventors: Grégory Mermoud, Veyras (CH); Jean-Philippe Vasseur, Anchorage, AK (US); Pierre-André Savalle, Rueil-Malmaison (FR)

(73) Assignee: Cisco Technology, Inc., San Jose, CA (US)

( * ) Notice: Subject to any disclaimer, the term of this patent is extended or adjusted under 35 U.S.C. 154(b) by 162 days.

(21) Appl. No.: 15/180,675

(22) Filed: Jun. 13, 2016

(65) Prior Publication Data
US 2017/0279830 A1    Sep. 28, 2017

Related U.S. Application Data

(60) Provisional application No. 62/312,678, filed on Mar. 24, 2016.

(51) Int. Cl.
*H04L 29/06* (2006.01)
*A61M 15/00* (2006.01)
(Continued)

(52) U.S. Cl.
CPC ....... *A61M 15/0086* (2013.01); *A61K 9/0073* (2013.01); *A61K 31/58* (2013.01); *A61M 11/008* (2014.02); *A61M 15/002* (2014.02); *A61M 15/009* (2013.01); *A61M 15/0021* (2014.02); *A61M 16/0003* (2014.02); *A61M 16/14* (2013.01); *G06F 19/3456* (2013.01); *H04L 63/1416* (2013.01); *H04L 63/1425* (2013.01); *H04L 63/1433* (2013.01); *H04L 63/1458* (2013.01); *H04L 67/02* (2013.01); *A61M 2202/064* (2013.01); *A61M 2210/065* (2013.01); *A61M 2210/0618* (2013.01); *A61M 2210/1028* (2013.01)

(58) Field of Classification Search
CPC ............. H04L 63/1416; H04L 63/1425; H04L 63/1433
See application file for complete search history.

(56) References Cited

U.S. PATENT DOCUMENTS

| 7,752,665 B1 | 7/2010 | Robertson et al. |
|---|---|---|
| 7,941,382 B2 | 5/2011 | Stokes et al. |

(Continued)

OTHER PUBLICATIONS

European Search Report in connection with European Application No. 17 16 2416.

*Primary Examiner* — Dao Q Ho
(74) *Attorney, Agent, or Firm* — Parker Ibrahim & Berg LLP; James M. Behmke; Stephen D. LeBarron

(57) ABSTRACT

In one embodiment, a device in a network detects an anomaly in the network by analyzing a set of sample data regarding one or more conditions of the network using a behavioral analytics model. The device receives feedback regarding the detected anomaly. The device determines that the anomaly was a true positive based on the received feedback. The device excludes the set of sample data from a training set for the behavioral analytics model, in response to determining that the anomaly was a true positive.

14 Claims, 10 Drawing Sheets

(51) Int. Cl.
  *H04L 29/08* (2006.01)
  *A61M 11/00* (2006.01)
  *A61M 16/00* (2006.01)
  *A61K 9/00* (2006.01)
  *A61K 31/58* (2006.01)
  *A61M 16/14* (2006.01)
  *G06F 19/00* (2018.01)

(56) References Cited

U.S. PATENT DOCUMENTS

| | | | |
|---|---|---|---|
| 8,554,703 B1 * | 10/2013 | Lin | G06N 99/005 |
| | | | 706/12 |
| 8,805,839 B2 | 8/2014 | Fitzgerald et al. | |
| 9,218,570 B2 | 12/2015 | Biem | |
| 2008/0109730 A1 * | 5/2008 | Coffman | G06Q 30/02 |
| | | | 715/733 |
| 2009/0103524 A1 * | 4/2009 | Mantripragada | H04L 65/1079 |
| | | | 370/352 |
| 2011/0078106 A1 | 3/2011 | Luchi et al. | |
| 2012/0047581 A1 * | 2/2012 | Banerjee | G06F 21/554 |
| | | | 726/24 |
| 2014/0279779 A1 | 9/2014 | Zou et al. | |
| 2015/0172303 A1 * | 6/2015 | Humble | H04L 63/1408 |
| | | | 726/23 |
| 2016/0078361 A1 | 3/2016 | Brueckner et al. | |
| 2016/0088006 A1 | 3/2016 | Gupta et al. | |

* cited by examiner

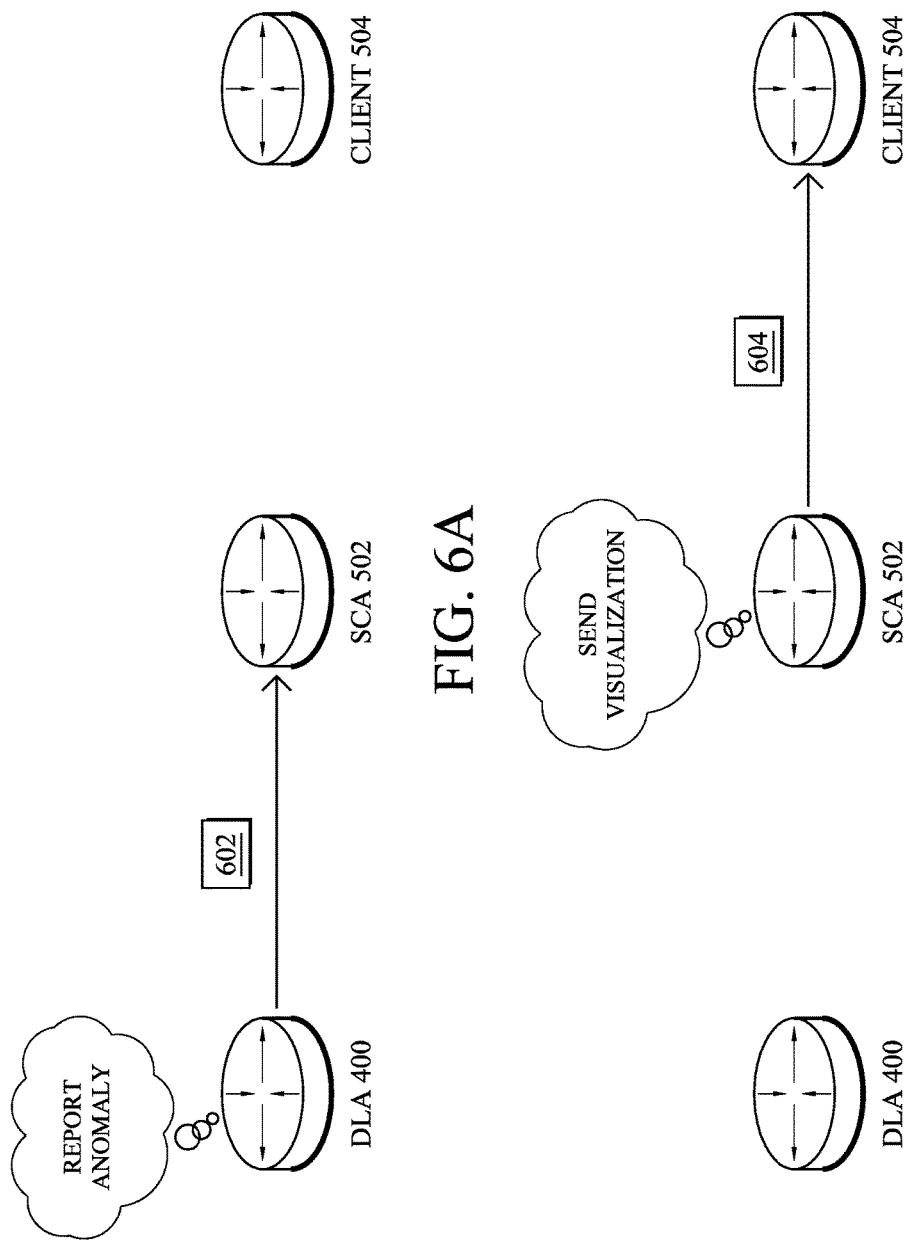

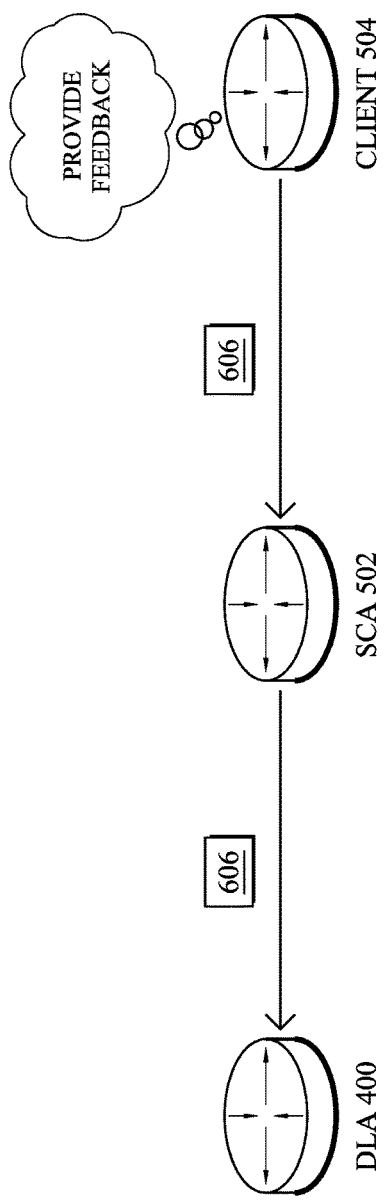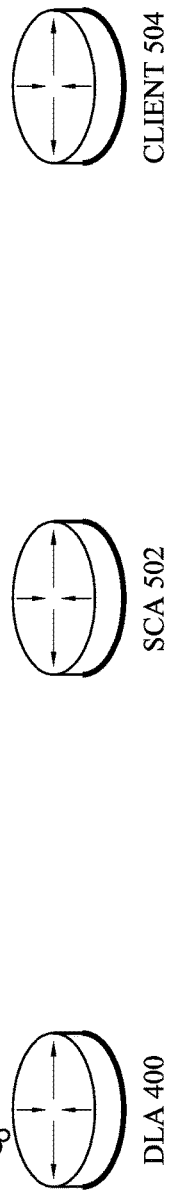
FIG. 6C
FIG. 6D

MECHANISMS TO PREVENT ANOMALY DETECTORS FROM LEARNING ANOMALOUS PATTERNS

RELATED APPLICATIONS

This application claims priority to U.S. Provisional Application No. 62/312,678, filed Mar. 24, 2016, entitled "MECHANISMS TO PREVENT ANOMALY DETECTORS FROM LEARNING ANOMALOUS PATTERNS," by Mermoud et al., the contents of which are hereby incorporated by reference.

TECHNICAL FIELD

The present disclosure relates generally to computer networks, and, more particularly, to preventing anomaly detectors from learning anomalous patterns.

BACKGROUND

Enterprise networks are carrying a very fast growing volume of both business and non-business critical traffic. Often, business applications such as video collaboration, cloud applications, etc., use the same hypertext transfer protocol (HTTP) and/or HTTP secure (HTTPS) techniques that are used by non-business critical web traffic. This complicates the task of optimizing network performance for specific applications, as many applications use the same protocols, thus making it difficult to distinguish and select traffic flows for optimization.

One type of network attack that is of particular concern in the context of computer networks is a Denial of Service (DoS) attack. In general, the goal of a DoS attack is to prevent legitimate use of the services available on the network. For example, a DoS jamming attack may artificially introduce interference into the network, thereby causing collisions with legitimate traffic and preventing message decoding. In another example, a DoS attack may attempt to overwhelm the network's resources by flooding the network with requests, to prevent legitimate requests from being processed. A DoS attack may also be distributed, to conceal the presence of the attack. For example, a distributed DoS (DDoS) attack may involve multiple attackers sending malicious requests, making it more difficult to distinguish when an attack is underway. When viewed in isolation, a particular one of such a request may not appear to be malicious. However, in the aggregate, the requests may overload a resource, thereby impacting legitimate requests sent to the resource.

An anomaly detector represents one mechanism to detect botnet-related traffic and other anomalies in a network. However, many types of anomaly detectors are prone to learning anomalous patterns over time as they occur in the network.

BRIEF DESCRIPTION OF THE DRAWINGS

The embodiments herein may be better understood by referring to the following description in conjunction with the accompanying drawings in which like reference numerals indicate identically or functionally similar elements, of which:

FIGS. 6A-6D illustrate an example of a DLA controlling the training set of an anomaly detection model;

DESCRIPTION OF EXAMPLE EMBODIMENTS

Overview

Figure 1A:
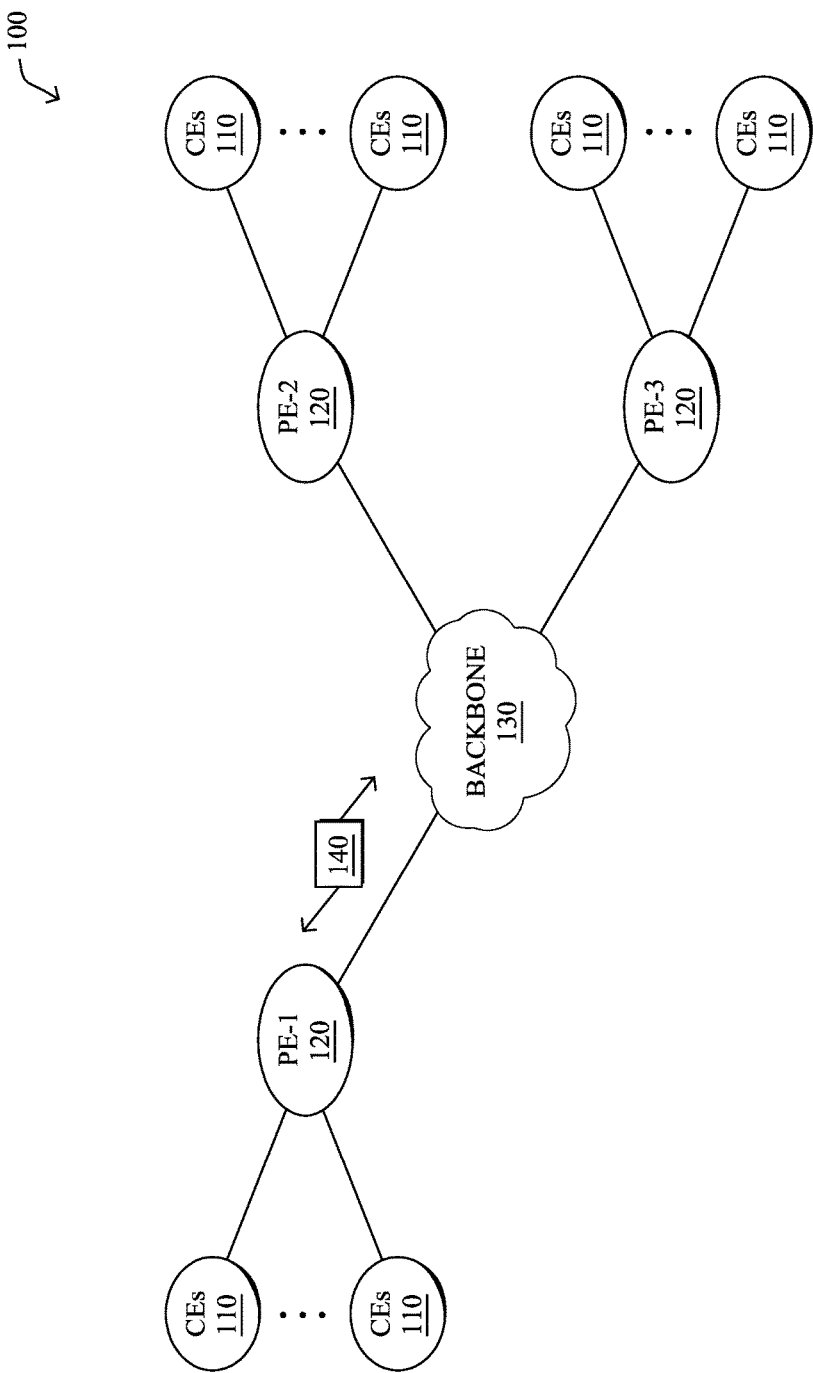
FIGS. 1A-1B illustrate an example communication network.

According to one or more embodiments of the disclosure, a device in a network detects an anomaly in the network by analyzing a set of sample data regarding one or more conditions of the network using a behavioral analytics model. The device receives feedback regarding the detected anomaly. The device determines that the anomaly was a true positive based on the received feedback. The device excludes the set of sample data from a training set for the behavioral analytics model, in response to determining that the anomaly was a true positive.

Description

A computer network is a geographically distributed collection of nodes interconnected by communication links and segments for transporting data between end nodes, such as personal computers and workstations, or other devices, such as sensors, etc. Many types of networks are available, with the types ranging from local area networks (LANs) to wide area networks (WANs). LANs typically connect the nodes over dedicated private communications links located in the same general physical location, such as a building or campus. WANs, on the other hand, typically connect geographically dispersed nodes over long-distance communications links, such as common carrier telephone lines, optical lightpaths, synchronous optical networks (SONET), or synchronous digital hierarchy (SDH) links, or Powerline Communications (PLC) such as IEEE 61334, IEEE P1901.2, and others. The Internet is an example of a WAN that connects disparate networks throughout the world, providing global communication between nodes on various networks. The nodes typically communicate over the network by exchanging discrete frames or packets of data according to predefined protocols, such as the Transmission Control Protocol/Internet Protocol (TCP/IP). In this context, a protocol consists of a set of rules defining how the nodes interact with each other. Computer networks may be further interconnected by an intermediate network node, such as a router, to extend the effective "size" of each network.

Smart object networks, such as sensor networks, in particular, are a specific type of network having spatially distributed autonomous devices such as sensors, actuators, etc., that cooperatively monitor physical or environmental conditions at different locations, such as, e.g., energy/power consumption, resource consumption (e.g., water/gas/etc. for advanced metering infrastructure or "AMI" applications) temperature, pressure, vibration, sound, radiation, motion, pollutants, etc. Other types of smart objects include actuators, e.g., responsible for turning on/off an engine or perform any other actions. Sensor networks, a type of smart object network, are typically shared-media networks, such as wireless or PLC networks. That is, in addition to one or more sensors, each sensor device (node) in a sensor network may generally be equipped with a radio transceiver or other communication port such as PLC, a microcontroller, and an energy source, such as a battery. Often, smart object networks are considered field area networks (FANs), neighborhood area networks (NANs), personal area networks (PANs), etc. Generally, size and cost constraints on smart object nodes (e.g., sensors) result in corresponding constraints on resources such as energy, memory, computational speed and bandwidth.

FIG. 1A is a schematic block diagram of an example computer network 100 illustratively comprising nodes/devices, such as a plurality of routers/devices interconnected by links or networks, as shown. For example, customer edge (CE) routers 110 may be interconnected with provider edge (PE) routers 120 (e.g., PE-1, PE-2, and PE-3) in order to communicate across a core network, such as an illustrative network backbone 130. For example, routers 110, 120 may be interconnected by the public Internet, a multiprotocol label switching (MPLS) virtual private network (VPN), or the like. Data packets 140 (e.g., traffic/messages) may be exchanged among the nodes/devices of the computer network 100 over links using predefined network communication protocols such as the Transmission Control Protocol/Internet Protocol (TCP/IP), User Datagram Protocol (UDP), Asynchronous Transfer Mode (ATM) protocol, Frame Relay protocol, or any other suitable protocol. Those skilled in the art will understand that any number of nodes, devices, links, etc. may be used in the computer network, and that the view shown herein is for simplicity.

In some implementations, a router or a set of routers may be connected to a private network (e.g., dedicated leased lines, an optical network, etc.) or a virtual private network (VPN), such as an MPLS VPN thanks to a carrier network, via one or more links exhibiting very different network and service level agreement characteristics. For the sake of illustration, a given customer site may fall under any of the following categories:

1.) Site Type A: a site connected to the network (e.g., via a private or VPN link) using a single CE router and a single link, with potentially a backup link (e.g., a 3G/4G/LTE backup connection). For example, a particular CE router 110 shown in network 100 may support a given customer site, potentially also with a backup link, such as a wireless connection.

2.) Site Type B: a site connected to the network using two MPLS VPN links (e.g., from different Service Providers), with potentially a backup link (e.g., a 3G/4G/LTE connection). A site of type B may itself be of different types:

2a.) Site Type B1: a site connected to the network using two MPLS VPN links (e.g., from different Service Providers), with potentially a backup link (e.g., a 3G/4G/LTE connection).

2b.) Site Type B2: a site connected to the network using one MPLS VPN link and one link connected to the public Internet, with potentially a backup link (e.g., a 3G/4G/LTE connection). For example, a particular customer site may be connected to network 100 via PE-3 and via a separate Internet connection, potentially also with a wireless backup link.

2c.) Site Type B3: a site connected to the network using two links connected to the public Internet, with potentially a backup link (e.g., a 3G/4G/LTE connection).

Notably, MPLS VPN links are usually tied to a committed service level agreement, whereas Internet links may either have no service level agreement at all or a loose service level agreement (e.g., a "Gold Package" Internet service connection that guarantees a certain level of performance to a customer site).

3.) Site Type C: a site of type B (e.g., types B1, B2 or B3) but with more than one CE router (e.g., a first CE router connected to one link while a second CE router is connected to the other link), and potentially a backup link (e.g., a wireless 3G/4G/LTE backup link). For example, a particular customer site may include a first CE router 110 connected to PE-2 and a second CE router 110 connected to PE-3.

Figure 1B:
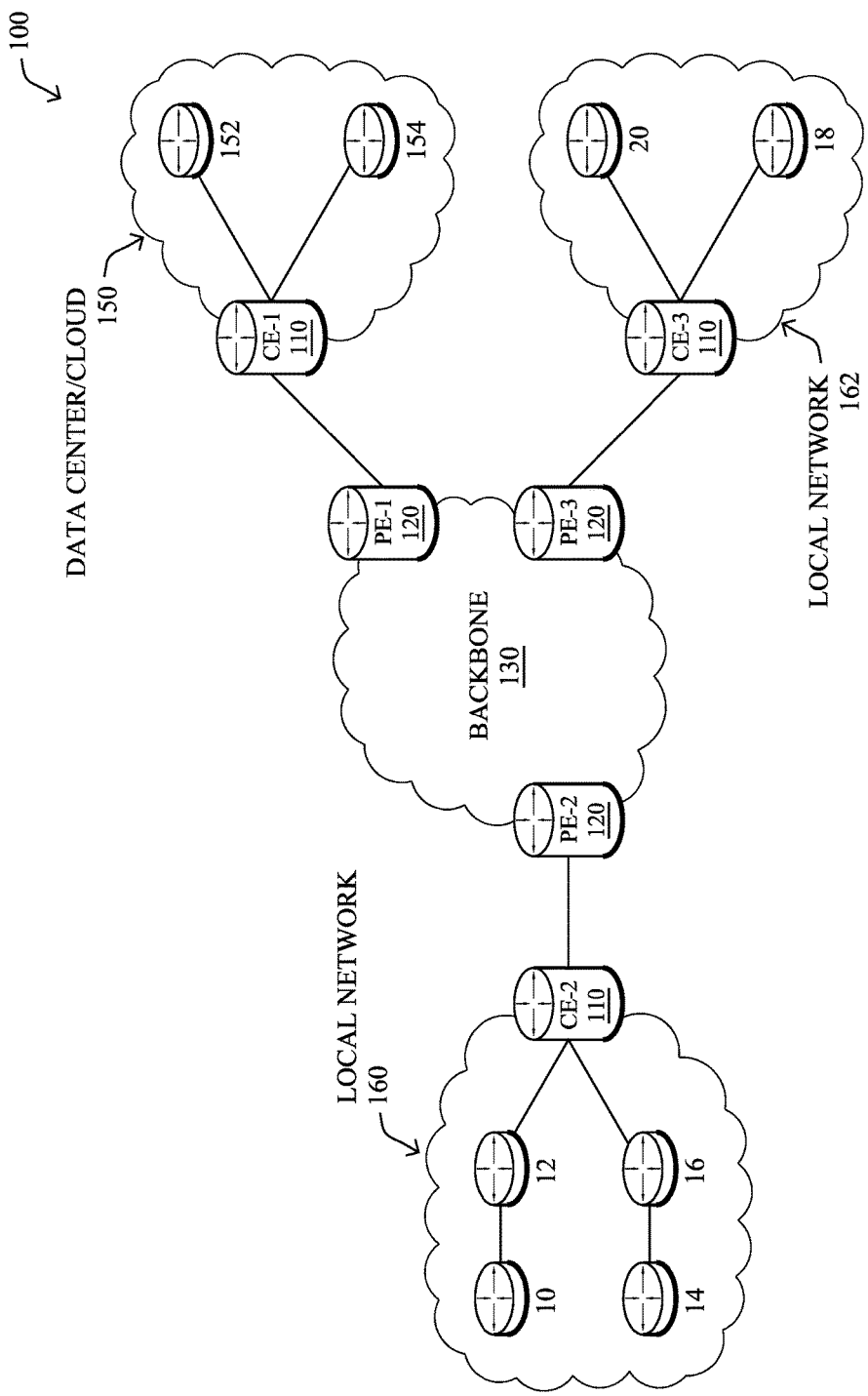

FIG. 1B illustrates an example of network 100 in greater detail, according to various embodiments. As shown, network backbone 130 may provide connectivity between devices located in different geographical areas and/or different types of local networks. For example, network 100 may comprise local/branch networks 160, 162 that include devices/nodes 10-16 and devices/nodes 18-20, respectively, as well as a data center/cloud environment 150 that includes servers 152-154. Notably, local networks 160-162 and data center/cloud environment 150 may be located in different geographic locations.

Servers 152-154 may include, in various embodiments, a network management server (NMS), a dynamic host configuration protocol (DHCP) server, a constrained application protocol (CoAP) server, an outage management system (OMS), an application policy infrastructure controller (APIC), an application server, etc. As would be appreciated, network 100 may include any number of local networks, data centers, cloud environments, devices/nodes, servers, etc.

In some embodiments, the techniques herein may be applied to other network topologies and configurations. For example, the techniques herein may be applied to peering points with high-speed links, data centers, etc.

In various embodiments, network 100 may include one or more mesh networks, such as an Internet of Things network. Loosely, the term "Internet of Things" or "IoT" refers to uniquely identifiable objects (things) and their virtual representations in a network-based architecture. In particular, the next frontier in the evolution of the Internet is the ability to connect more than just computers and communications devices, but rather the ability to connect "objects" in general, such as lights, appliances, vehicles, heating, ventilating, and air-conditioning (HVAC), windows and window shades and blinds, doors, locks, etc. The "Internet of Things" thus generally refers to the interconnection of objects (e.g., smart objects), such as sensors and actuators, over a computer network (e.g., via IP), which may be the public Internet or a private network.

Notably, shared-media mesh networks, such as wireless or PLC networks, etc., are often on what is referred to as Low-Power and Lossy Networks (LLNs), which are a class of network in which both the routers and their interconnect are constrained: LLN routers typically operate with constraints, e.g., processing power, memory, and/or energy (battery), and their interconnects are characterized by, illustratively, high loss rates, low data rates, and/or instability. LLNs are comprised of anything from a few dozen to thousands or even millions of LLN routers, and support point-to-point traffic (between devices inside the LLN), point-to-multipoint traffic (from a central control point such at the root node to a subset of devices inside the LLN), and multipoint-to-point traffic (from devices inside the LLN towards a central control point). Often, an IoT network is implemented with an LLN-like architecture. For example, as shown, local network 160 may be an LLN in which CE-2 operates as a root node for nodes/devices 10-16 in the local mesh, in some embodiments.

In contrast to traditional networks, LLNs face a number of communication challenges. First, LLNs communicate over a physical medium that is strongly affected by environmental conditions that change over time. Some examples include temporal changes in interference (e.g., other wireless networks or electrical appliances), physical obstructions (e.g., doors opening/closing, seasonal changes such as the foliage density of trees, etc.), and propagation characteristics of the physical media (e.g., temperature or humidity changes, etc.). The time scales of such temporal changes can range between milliseconds (e.g., transmissions from other transceivers) to months (e.g., seasonal changes of an outdoor environment). In addition, LLN devices typically use low-cost and low-power designs that limit the capabilities of their transceivers. In particular, LLN transceivers typically provide low throughput. Furthermore, LLN transceivers typically support limited link margin, making the effects of interference and environmental changes visible to link and network protocols. The high number of nodes in LLNs in comparison to traditional networks also makes routing, quality of service (QoS), security, network management, and traffic engineering extremely challenging, to mention a few.

Figure 2:
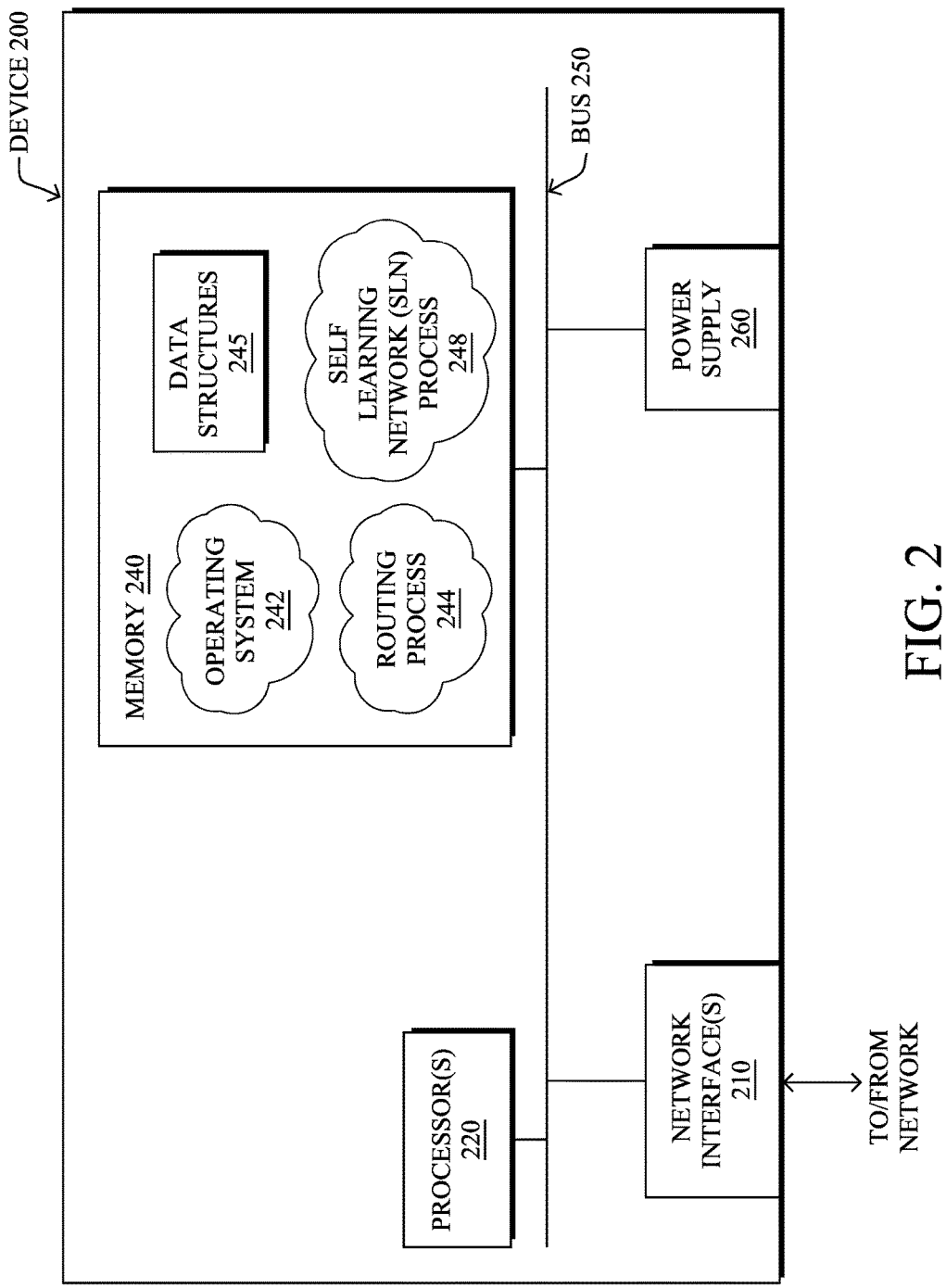
FIG. 2 illustrates an example network device/node.

FIG. 2 is a schematic block diagram of an example node/device 200 that may be used with one or more embodiments described herein, e.g., as any of the computing devices shown in FIGS. 1A-1B, particularly the PE routers 120, CE routers 110, nodes/device 10-20, servers 152-154 (e.g., a network controller located in a data center, etc.), any other computing device that supports the operations of network 100 (e.g., switches, etc.), or any of the other devices referenced below. The device 200 may also be any other suitable type of device depending upon the type of network architecture in place, such as IoT nodes, etc. Device 200 comprises one or more network interfaces 210, one or more processors 220, and a memory 240 interconnected by a system bus 250, and is powered by a power supply 260.

The network interfaces 210 include the mechanical, electrical, and signaling circuitry for communicating data over physical links coupled to the network 100. The network interfaces may be configured to transmit and/or receive data using a variety of different communication protocols. Notably, a physical network interface 210 may also be used to implement one or more virtual network interfaces, such as for virtual private network (VPN) access, known to those skilled in the art.

The memory 240 comprises a plurality of storage locations that are addressable by the processor(s) 220 and the network interfaces 210 for storing software programs and data structures associated with the embodiments described herein. The processor 220 may comprise necessary elements or logic adapted to execute the software programs and manipulate the data structures 245. An operating system 242 (e.g., the Internetworking Operating System, or IOS®, of Cisco Systems, Inc., another operating system, etc.), portions of which are typically resident in memory 240 and executed by the processor(s), functionally organizes the node by, inter alia, invoking network operations in support of software processors and/or services executing on the device. These software processors and/or services may comprise routing process 244 (e.g., routing services) and illustratively, a self learning network (SLN) process 248, as described herein, any of which may alternatively be located within individual network interfaces.

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules configured to operate in accordance with the techniques herein (e.g., according to the functionality of a similar process). Further, while processes may be shown and/or described separately, those skilled in the art will appreciate that processes may be routines or modules within other processes.

Routing process/services 244 include computer executable instructions executed by processor 220 to perform functions provided by one or more routing protocols, such as the Interior Gateway Protocol (IGP) (e.g., Open Shortest Path First, "OSPF," and Intermediate-System-to-Intermediate-System, "IS-IS"), the Border Gateway Protocol (BGP), etc., as will be understood by those skilled in the art. These functions may be configured to manage a forwarding information database including, e.g., data used to make forwarding decisions. In particular, changes in the network topology may be communicated among routers 200 using routing protocols, such as the conventional OSPF and IS-IS link-state protocols (e.g., to "converge" to an identical view of the network topology).

Notably, routing process 244 may also perform functions related to virtual routing protocols, such as maintaining VRF instance, or tunneling protocols, such as for MPLS, generalized MPLS (GMPLS), etc., each as will be understood by those skilled in the art. Also, EVPN, e.g., as described in the IETF Internet Draft entitled "BGP MPLS Based Ethernet VPN" <draft-ietf-l2vpn-evpn>, introduce a solution for multipoint L2VPN services, with advanced multi-homing capabilities, using BGP for distributing customer/client media access control (MAC) address reach-ability information over the core MPLS/IP network.

SLN process 248 includes computer executable instructions that, when executed by processor(s) 220, cause device 200 to perform anomaly detection functions as part of an anomaly detection infrastructure within the network. In general, anomaly detection attempts to identify patterns that do not conform to an expected behavior. For example, in one embodiment, the anomaly detection infrastructure of the network may be operable to detect network attacks (e.g., DDoS attacks, the use of malware such as viruses, rootkits, etc.). However, anomaly detection in the context of computer networking typically presents a number of challenges: 1.) a lack of a ground truth (e.g., examples of normal vs. abnormal network behavior), 2.) being able to define a "normal" region in a highly dimensional space can be challenging, 3.) the dynamic nature of the problem due to changing network behaviors/anomalies, 4.) malicious behaviors such as malware, is viruses, rootkits, etc. may adapt in order to appear "normal," and 5.) differentiating between noise and relevant anomalies is not necessarily possible from a statistical standpoint, but typically also requires domain knowledge.

Anomalies may also take a number of forms in a computer network: 1.) point anomalies (e.g., a specific data point is abnormal compared to other data points), 2.) contextual anomalies (e.g., a data point is abnormal in a specific context but not when taken individually), or 3.) collective anomalies (e.g., a collection of data points is abnormal with regards to an entire set of data points). Generally, anomaly detection refers to the ability to detect an anomaly that could be triggered by the presence of malware attempting to access data (e.g., data exfiltration), spyware, ransom-ware, etc. and/or non-malicious anomalies such as misconfigurations or misbehaving code. Particularly, an anomaly may be raised in a number of circumstances:

Security threats: the presence of a malware using unknown attacks patterns (e.g., no static signatures) may lead to modifying the behavior of a host in terms of traffic patterns, graphs structure, etc. Machine learning processes may detect these types of anomalies using advanced approaches capable of modeling subtle changes or correlation between changes (e.g., unexpected behavior) in a highly dimensional space. Such anomalies are raised in order to detect, e.g., the presence of a 0-day malware, malware used to perform data ex-filtration thanks to a Command and Control (C2) channel, or even to trigger (Distributed) Denial of Service (DoS) such as DNS reflection, UDP flood, HTTP recursive get, etc. In the case of a (D)DoS, although technical an anomaly, the term "DoS" is usually used. SLN process 248 may detect malware based on the corresponding impact on traffic, host models, graph-based analysis, etc., when the malware attempts to connect to a C2 channel, attempts to move laterally, or exfiltrate information using various techniques.

Misbehaving devices: a device such as a laptop, a server of a network device (e.g., storage, router, switch, printer, etc.) may misbehave in a network for a number of reasons: 1.) a user using a discovery tool that performs (massive) undesirable scanning in the network (in contrast with a lawful scanning by a network management tool performing device discovery), 2.) a software defect (e.g. a switch or router dropping packet because of a corrupted RIB/FIB or the presence of a persistent loop by a routing protocol hitting a corner case).

Dramatic behavior change: the introduction of a new networking or end-device configuration, or even the introduction of a new application may lead to dramatic behavioral changes. Although technically not anomalous, an SLN-enabled node having computed behavioral model(s) may raise an anomaly when detecting a brutal behavior change. Note that in such as case, although an anomaly may be raised, a learning system such as SLN is expected to learn the new behavior and dynamically adapts according to potential user feedback.

Misconfigured devices: a configuration change may trigger an anomaly: a misconfigured access control list (ACL), route redistribution policy, routing policy, QoS policy maps, or the like, may have dramatic consequences such a traffic black-hole, QoS degradation, etc. SLN process 248 may advantageously identify these forms of misconfigurations, in order to be detected and fixed.

In various embodiments, SLN process 248 may utilize machine learning techniques, to perform anomaly detection in the network. In general, machine learning is concerned with the design and the development of techniques that take as input empirical data (such as network statistics and performance indicators), and recognize complex patterns in these data. One very common pattern among machine learning techniques is the use of an underlying model M, whose parameters are optimized for minimizing the cost function associated to M, given the input data. For instance, in the context of classification, the model M may be a straight line that separates the data into two classes (e.g., labels) such that $M=a*x+b*y+c$ and the cost function would be the number of misclassified points. The learning process then operates by adjusting the parameters a, b, c such that the number of misclassified points is minimal. After this optimization phase (or learning phase), the model M can be used very easily to classify new data points. Often, M is a statistical model, and the cost function is inversely proportional to the likelihood of M, given the input data.

Computational entities that rely on one or more machine learning techniques to perform a task for which they have not been explicitly programmed to perform are typically referred to as learning machines. In particular, learning machines are capable of adjusting their behavior to their environment. For example, a learning machine may dynamically make future predictions based on current or prior network measurements, may make control decisions based on the effects of prior control commands, etc.

For purposes of anomaly detection in a network, a learning machine may construct a model of normal network behavior, to detect data points that deviate from this model. For example, a given model (e.g., a supervised, un-supervised, or semi-supervised model) may be used to generate and report anomaly scores to another device. Example machine learning techniques that may be used to construct and analyze such a model may include, but are not limited to, nearest neighbor (NN) techniques (e.g., k-NN models, replicator NN models, etc.), statistical techniques (e.g., Bayesian networks, etc.), clustering techniques (e.g., k-means, etc.), neural networks (e.g., reservoir networks, artificial neural networks, etc.), support vector machines (SVMs), or the like.

One class of machine learning techniques that is of particular use in the context of anomaly detection is clustering. Generally speaking, clustering is a family of techniques that seek to group data according to some typically predefined notion of similarity. For instance, clustering is a very popular technique used in recommender systems for grouping objects that are similar in terms of people's taste (e.g., because you watched X, you may be interested in Y, etc.). Typical clustering algorithms are k-means, density based spatial clustering of applications with noise (DBSCAN) and mean-shift, where a distance to a cluster is computed with the hope of reflecting a degree of anomaly (e.g., using a Euclidean distance and a cluster based local outlier factor that takes into account the cluster density).

Replicator techniques may also be used for purposes of anomaly detection. Such techniques generally attempt to replicate an input in an unsupervised manner by projecting the data into a smaller space (e.g., compressing the space, thus performing some dimensionality reduction) and then reconstructing the original input, with the objective of keeping the "normal" pattern in the low dimensional space. Example techniques that fall into this category include principal component analysis (PCA) (e.g., for linear models), multi-layer perceptron (MLP) ANNs (e.g., for non-linear models), and replicating reservoir networks (e.g., for non-linear models, typically for time series).

According to various embodiments, SLN process 248 may also use graph-based models for purposes of anomaly detection. Generally speaking, a graph-based model attempts to represent the relationships between different entities as a graph of nodes interconnected by edges. For example, ego-centric graphs have been used to represent the relationship between a particular social networking profile and the other profiles connected to it (e.g., the connected "friends" of a user, etc.). The patterns of these connections can then be analyzed for purposes of anomaly detection. For example, in the social networking context, it may be considered anomalous for the connections of a particular profile not to share connections, as well. In other words, a person's social connections are typically also interconnected. If no such interconnections exist, this may be deemed anomalous.

Figure 3:
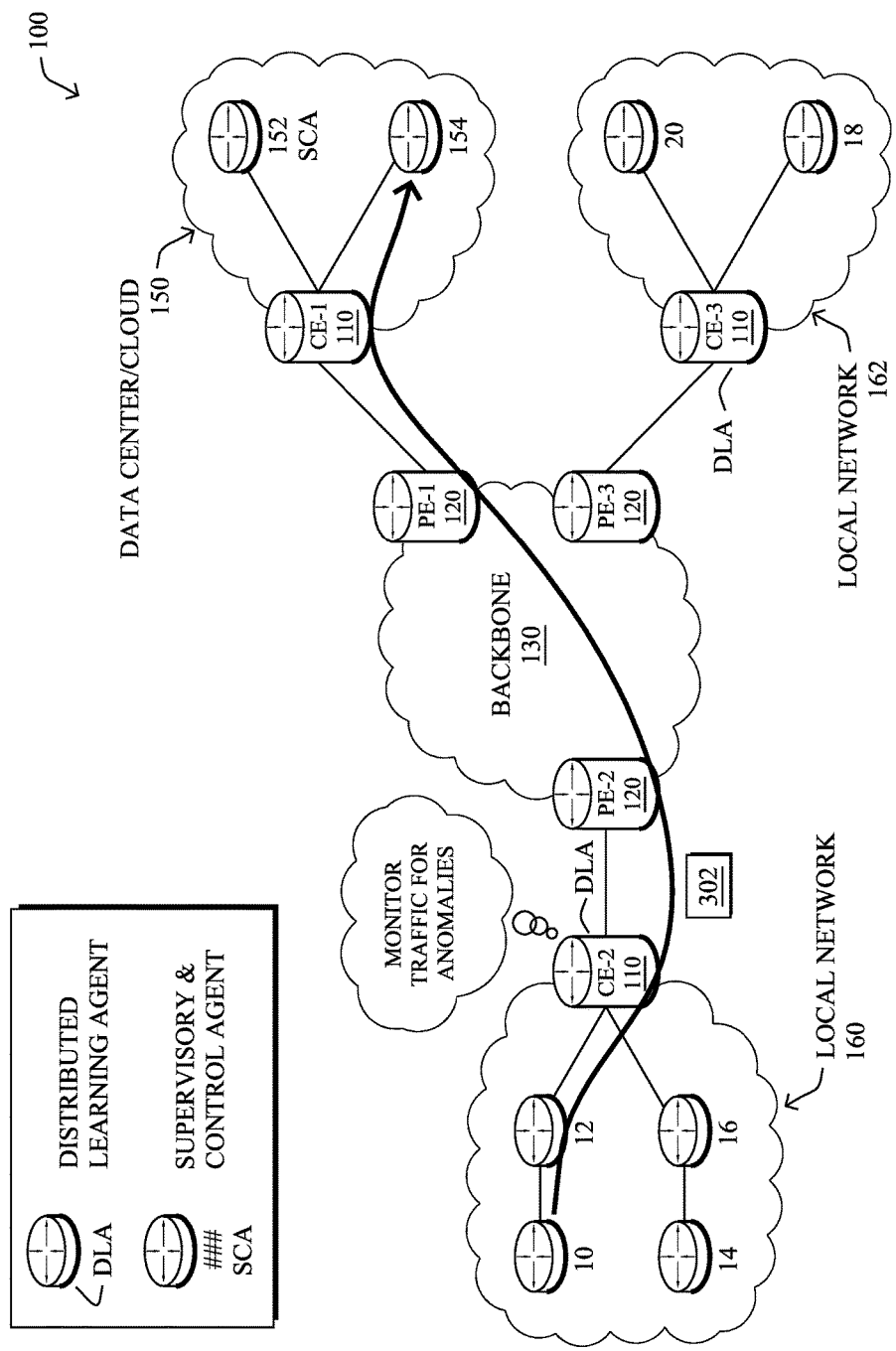
FIG. 3 illustrates an example self learning network (SLN) infrastructure.

An example self learning network (SLN) infrastructure that may be used to detect network anomalies is shown in FIG. 3, according to various embodiments. Generally, network devices may be configured to operate as part of an SLN infrastructure to detect, analyze, and/or mitigate network anomalies such as network attacks (e.g., by executing SLN process 248). Such an infrastructure may include certain network devices acting as distributed learning agents (DLAs) and one or more supervisory/centralized devices acting as a supervisory and control agent (SCA). A DLA may be operable to monitor network conditions (e.g., router states, traffic flows, etc.), perform anomaly detection on the monitored data using one or more machine learning models, report detected anomalies to the SCA, and/or perform local mitigation actions. Similarly, an SCA may be operable to coordinate the deployment and configuration of the DLAs (e.g., by downloading software upgrades to a DLA, etc.), receive information from the DLAs (e.g., detected anomalies/attacks, compressed data for visualization, etc.), provide information regarding a detected anomaly to a user interface (e.g., by providing a webpage to a display, etc.), and/or analyze data regarding a detected anomaly using more CPU intensive machine learning processes.

One type of network attack that is of particular concern in the context of computer networks is a Denial of Service (DoS) attack. In general, the goal of a DoS attack is to prevent legitimate use of the services available on the network. For example, a DoS jamming attack may artificially introduce interference into the network, thereby causing collisions with legitimate traffic and preventing message decoding. In another example, a DoS attack may attempt to overwhelm the network's resources by flooding the network with requests (e.g., SYN flooding, sending an overwhelming number of requests to an HTTP server, etc.), to prevent legitimate requests from being processed. A DoS attack may also be distributed, to conceal the presence of the attack. For example, a distributed DoS (DDoS) attack may involve multiple attackers sending malicious requests, making it more difficult to distinguish when an attack is underway. When viewed in isolation, a particular one of such a request may not appear to be malicious. However, in the aggregate, the requests may overload a resource, thereby impacting legitimate requests sent to the resource.

Botnets represent one way in which a DDoS attack may be launched against a network. In a botnet, a subset of the network devices may be infected with malicious software, thereby allowing the devices in the botnet to be controlled by a single master. Using this control, the master can then coordinate the attack against a given network resource.

DoS attacks are relatively easy to detect when they are brute-force (e.g. volumetric), but, especially when highly distributed, they may be difficult to distinguish from a flash-crowd (e.g., an overload of the system due to many legitimate users accessing it at the same time). This fact, in conjunction with the increasing complexity of performed attacks, makes the use of "classic" (usually threshold-based) techniques useless for detecting them. However, machine learning techniques may still be able to detect such attacks, before the network or service becomes unavailable. For example, some machine learning approaches may analyze changes in the overall statistical behavior of the network traffic (e.g., the traffic distribution among flow flattens when a DDoS attack based on a number of microflows happens). Other approaches may attempt to statistically characterizing the normal behaviors of network flows or TCP connections, in order to detect significant deviations. Classification approaches try to extract features of network flows and traffic that are characteristic of normal traffic or malicious traffic, constructing from these features a classifier that is able to differentiate between the two classes (normal and malicious).

As shown in FIG. 3, routers CE-2 and CE-3 may be configured as DLAs and server 152 may be configured as an SCA, in one implementation. In such a case, routers CE-2 and CE-3 may monitor traffic flows, router states (e.g., queues, routing tables, etc.), or any other conditions that may be indicative of an anomaly in network 100. As would be appreciated, any number of different types of network devices may be configured as a DLA (e.g., routers, switches, servers, blades, etc.) or as an SCA.

Assume, for purposes of illustration, that CE-2 acts as a DLA that monitors traffic flows associated with the devices of local network 160 (e.g., by comparing the monitored conditions to one or more machine-learning models). For example, assume that device/node 10 sends a particular traffic flow 302 to server 154 (e.g., an application server, etc.). In such a case, router CE-2 may monitor the packets of traffic flow 302 and, based on its local anomaly detection mechanism, determine that traffic flow 302 is anomalous. Anomalous traffic flows may be incoming, outgoing, or internal to a local network serviced by a DLA, in various cases.

In some cases, traffic 302 may be associated with a particular application supported by network 100. Such applications may include, but are not limited to, automation applications, control applications, voice applications, video applications, alert/notification applications (e.g., monitoring applications), communication applications, and the like. For example, traffic 302 may be email traffic, HTTP traffic, traffic associated with an enterprise resource planning (ERP) application, etc.

In various embodiments, the anomaly detection mechanisms in network 100 may use Internet Behavioral Analytics (IBA). In general, IBA refers to the use of advanced analytics coupled with networking technologies, to detect anomalies in the network. Although described later with greater details, the ability to model the behavior of a device (networking switch/router, host, etc.) will allow for the detection of malware, which is complementary to the use of a firewall that uses static signatures. Observing behavioral changes (e.g., a deviation from modeled behavior) thanks to aggregated flows records, deep packet inspection, etc., may allow detection of an anomaly such as an horizontal movement (e.g. propagation of a malware, etc.), or an attempt to perform information exfiltration.

Figure 4:
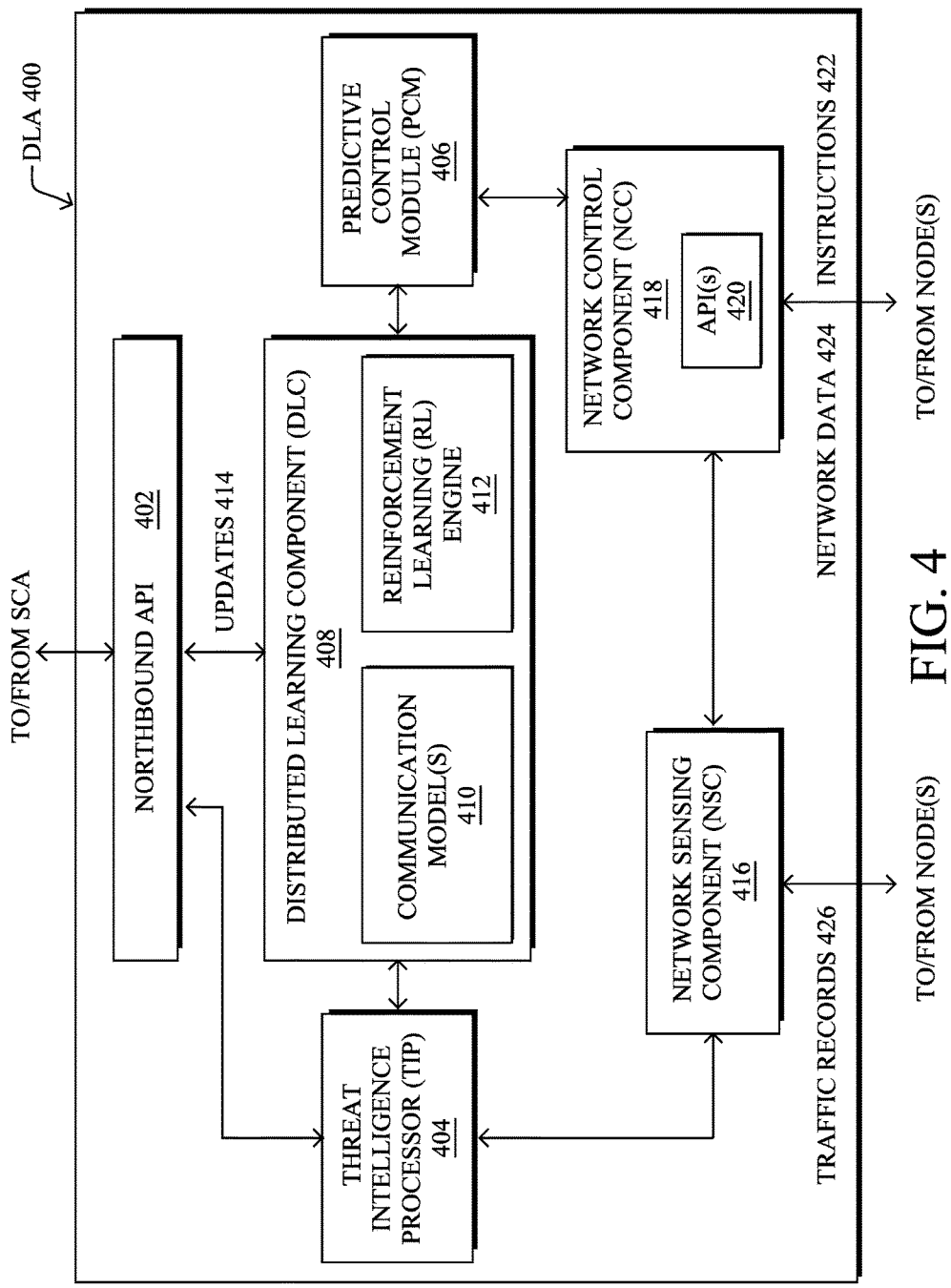
FIG. 4 illustrates an example distributed learning agent (DLA)

FIG. 4 illustrates an example distributed learning agent (DLA) 400 in greater detail, according to various embodiments. Generally, a DLA may comprise a series of modules hosting sophisticated tasks (e.g., as part of an overall SLN process 248). Generally, DLA 400 may communicate with an SCA (e.g., via one or more northbound APIs 402) and any number of nodes/devices in the portion of the network associated with DLA 400 (e.g., via APIs 420, etc.).

In some embodiments, DLA 400 may execute a Network Sensing Component (NSC) 416 that is a passive sensing construct used to collect a variety of traffic record inputs 426 from monitoring mechanisms deployed to the network nodes. For example, traffic record inputs 426 may include Cisco™ Netflow records or other traffic information, application identification information from a Cisco™ Network Based Application Recognition (NBAR) process or another application-recognition mechanism, administrative information from an administrative reporting tool (ART), local network state information service sets, media metrics, raw packets, or the like.

Furthermore, NSC 416 may be configured to dynamically employ Deep Packet Inspection (DPI), to enrich the mathematical models computed by DLA 400, a critical source of information to detect a number of anomalies. Also of note is that accessing control/data plane data may be of utmost importance, to detect a number of advanced threats such as data exfiltration. NSC 416 may be configured to perform data analysis and data enhancement (e.g., the addition of valuable information to the raw data through correlation of different information sources). Moreover, NSC 416 may compute various networking based metrics for use by the Distributed Learning Component (DLC) 408, such as a large number of statistics, some of which may not be directly interpretable by a human.

In some embodiments, DLA 400 may also include DLC 408 that may perform a number of key operations such as any or all of the following: computation of Self Organizing Learning Topologies (SOLT), computation of "features" (e.g., feature vectors), advanced machine learning processes, etc., which DLA 400 may use in combination to perform a specific set of tasks. In some cases, DLC 408 may include a reinforcement learning (RL) engine 412 that uses reinforcement learning to detect anomalies or otherwise assess the operating conditions of the network. Accordingly, RL engine 412 may maintain and/or use any number of communication models 410 that model, e.g., various flows of traffic in the network. In further embodiments, DLC 408 may use any other form of machine learning techniques, such as those described previously (e.g., supervised or unsupervised techniques, etc.). For example, in the context of SLN for security, DLC 408 may perform modeling of traffic and applications in the area of the network associated with DLA 400. DLC 408 can then use the resulting models 410 to detect graph-based and other forms of anomalies (e.g., by comparing the models with current network characteristics, such as traffic patterns. The SCA may also send updates 414 to DLC 408 to update model(s) 410 and/or RL engine 412 (e.g., based on information from other deployed DLAs, input from a user, etc.).

When present, RL engine 412 may enable a feed-back loop between the system and the end user, to automatically adapt the system decisions to the expectations of the user and raise anomalies that are of interest to the user (e.g., as received via a user interface of the SCA). In one embodiment, RL engine 412 may receive a signal from the user in the form of a numerical reward that represents for example the level of interest of the user related to a previously raised event. Consequently the agent may adapt its actions (e.g. search for new anomalies), to maximize its reward over time, thus adapting the system to the expectations of the user. More specifically, the user may optionally provide feedback thanks to a lightweight mechanism (e.g., 'like' or 'dislike') via the user interface.

In some cases, DLA 400 may include a threat intelligence processor (TIP) 404 that processes anomaly characteristics so as to further assess the relevancy of the anomaly (e.g. the applications involved in the anomaly, location, scores/degree of anomaly for a given model, nature of the flows, or the like). TIP 404 may also generate or otherwise leverage a machine learning-based model that computes a relevance index. Such a model may be used across the network to select/prioritize anomalies according to the relevancies.

DLA 400 may also execute a Predictive Control Module (PCM) 406 that triggers relevant actions in light of the events detected by DLC 408. In order words, PCM 406 is the decision maker, subject to policy. For example, PCM 406 may employ rules that control when DLA 400 is to send information to the SCA (e.g., alerts, predictions, recommended actions, trending data, etc.) and/or modify a network behavior itself. For example, PCM 406 may determine that a particular traffic flow should be blocked (e.g., based on the assessment of the flow by TIP 404 and DLC 408) and an alert sent to the SCA.

Network Control Component (NCC) 418 is a module configured to trigger any of the actions determined by PCM 406 in the network nodes associated with DLA 400. In various embodiments, NCC 418 may communicate the corresponding instructions 422 to the network nodes using APIs 420 (e.g., DQoS interfaces, ABR interfaces, DCAC interfaces, etc.). For example, NCC 418 may send mitigation instructions 422 to one or more nodes that instruct the receives to reroute certain anomalous traffic, perform traffic shaping, drop or otherwise "black hole" the traffic, or take other mitigation steps. In some embodiments, NCC 418 may also be configured to cause redirection of the traffic to a "honeypot" device for forensic analysis. Such actions may be user-controlled, in some cases, through the use of policy maps and other configurations. Note that NCC 418 may be accessible via a very flexible interface allowing a coordinated set of sophisticated actions. In further embodiments, API(s) 420 of NCC 418 may also gather/receive certain network data 424 from the deployed nodes such as Cisco™ OnePK information or the like.

The various components of DLA 400 may be executed within a container, in some embodiments, that receives the various data records and other information directly from the host router or other networking device. Doing so prevents these records from consuming additional bandwidth in the external network. This is a major advantage of such a distributed system over centralized approaches that require sending large amount of traffic records. Furthermore, the above mechanisms afford DLA 400 additional insight into other information such as control plane packet and local network states that are only available on premise. Note also that the components shown in FIG. 4 may have a low footprint, both in terms of memory and CPU. More specifically, DLA 400 may use lightweight techniques to compute features, identify and classify observation data, and perform other functions locally without significantly impacting the functions of the host router or other networking device.

As noted above, model(s) 410 may include statistical models that rely on the notion of statistical likelihood to determine whether a specific event is anomalous or not. Most anomaly detection processes of this type work by modeling a distribution f(X) of historical data where X is a so-called feature vector in $R^n$ whose dimensions are the n features that quantify different network behaviors. Then, each new event i can be scored as the conditional probability $p=P(X_i|X_1, X_2, \ldots, X_{i-1})$, that is, the probability that $X_i$ occurs, given previous observations $X_1$ to $X_{i-1}$. An anomaly is then raised when p is "small enough," meaning that the probability of the actual event occurring is below a threshold such that occurrence of the event is considered unlikely/anomalous.

One of the key issues with the above approach is that the first occurrence of an attack may generate a series of n samples $X_j, \ldots, X_{j+n}$ that will be detected as a statistical anomaly, but further occurrences will see their likelihood increase as a result of the integration of the samples $X_j, \ldots, X_{j+n}$ in the underlying model. In other words, if the statistical model continues to include anomalous sets of sample data in its training set, the model will adapt its output probabilities accordingly, leading to the result that the model may eventually consider attack/anomalous conditions as the new normal.

Mechanisms to Prevent Anomaly Detectors from Learning Anomalous Patterns

The techniques herein propose mechanisms to prevent anomaly detection models to be biased by prior occurrences of attacks, malware, intrusions, or other events that should be deemed anomalous. In some aspects, the mechanisms delay and/or revert the training of the underlying model with samples from a confirmed anomaly. Further, the mechanisms may prevent the anomaly detection system from being affected by previous occurrences of anomalies that are deemed relevant by the user (e.g., confirmed as being true positives). Conversely, similar mechanisms are introduced to accelerate the learning of events that are deemed irrelevant by the user, so as to avoid detection in the future.

Specifically, according to one or more embodiments of the disclosure as described in detail below, a device in a network detects an anomaly in the network by analyzing a set of sample data regarding one or more conditions of the network using a behavioral analytics model. The device receives feedback regarding the detected anomaly. The device determines that the anomaly was a true positive based on the received feedback. The device excludes the set of sample data from a training set for the behavioral analytics model, in response to determining that the anomaly was a true positive.

Illustratively, the techniques described herein may be performed by hardware, software, and/or firmware, such as in accordance with the SLN process 248, which may include computer executable instructions executed by the processor 220 (or independent processor of interfaces 210) to perform functions relating to the techniques described herein, e.g., in conjunction with routing process 244.

Figure 5:
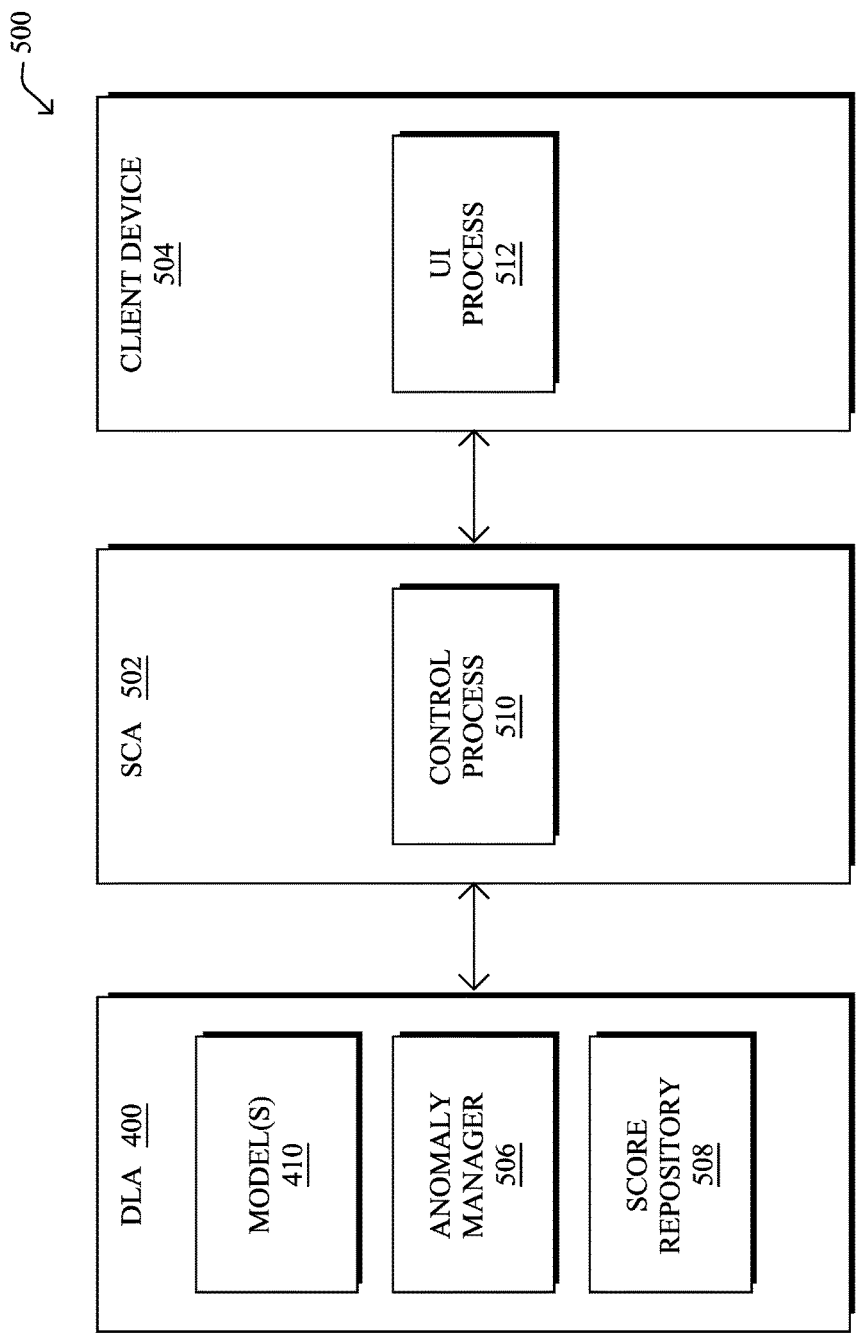
FIG. 5 illustrates an example system architecture for controlling the training of an anomaly detector.

Operationally, FIG. 5 illustrates an example system architecture 500 for controlling the training of an anomaly detector, according to various embodiments. As shown, architecture 500 may include a DLA 400, an SCA 502, and potentially a client device 504 in communication therewith.

As described above, SCA 502 may execute a control process 510 that provides supervisory control over DLA 400 and receives notifications of any anomalies detected by DLA 400. For example, control process 510 may receive administrative commands and/or parameters from a user interface (UI) process 512 executed by client device 504 or directly on SCA 502. Notably, control process 510 may generate visualizations for display by UI process 512, thereby allowing an administrator or other user to review the anomaly detection mechanisms in the network. In response, the user may provide feedback regarding any detected anomalies to DLA 400 via control process 510.

Also as described above, DLA 400 may generate and use any number of behavioral analytics models 410, to detect anomalous conditions in the network. These models may be based on any number of sets of sample data regarding the operation of the network (e.g., characteristics of the traffic flows in the network, metrics derived therefrom, etc.). In other words, a given model 410 may use a training set of n-number of prior sets of samples, to determine whether the next set of sample data represents an anomaly in the network. For example, a statistical model may evaluate the probability of an observed event occurring in the network, given the training set of prior observations regarding the network. If the probability of the observed event occurring is below a threshold, DLA 400 may determine that an anomaly has occurred and store an anomaly score for the anomaly in a score repository 508 based on the probability of the anomalous event.

According to various embodiments, the techniques herein introduce a mechanism whereby the training of model(s) 410 is delegated by a module called the Anomaly Manager 506 hosted by DLA 400 (e.g., as part of DLC 408 or as a standalone module). Anomaly manager 506 may receive a stream of samples $X_i$, $X_{i+1}$, etc. along with the corresponding scores $P_i=P(X_i|X_1, X_2, \ldots, X_{i-1})$ etc. from model(s) 410. If anomaly manager 506 deems these scores sufficient to trigger/raise an anomaly, anomaly manager 506 may store the scores and potentially the set of sample data that triggered the anomaly in score repository 508. Doing so allows DLA 400 to retain details about the anomaly until the user of UI process 512 has the opportunity to review the anomaly. If not, the corresponding samples are directly used to train the behavioral analytics model 410.

FIGS. 6A-6D illustrate an example of DLA 400 controlling the training set of anomaly detection model 410, in various embodiments. As shown in FIG. 6A, assume that DLA 400 detects an anomaly by analyzing a set of sample data regarding traffic in the network using the statistical model. If DLA 400 determines that an anomaly has been detected based on this analysis, DLA 400 may cache information regarding the anomaly (e.g., in repository 508) and send an anomaly notification 602 to SCA 502 to report the anomaly. Notification 602 may include any or all of the information regarding the detected anomaly. For example, notification 602 may include the set of sample data that triggered the anomaly detection, information derived therefrom, the anomaly score, a time or date associated with the detected anomaly, or other such information.

As shown in FIG. 6B, SCA 502 may use the data in anomaly notification 602 to provide a visualization 604 to UI process 512 of client device 504. Visualization 504 may also include additional information to help the user of client device 504 to assess the detected anomaly. For example, visualization 504 may include a representation of the network topology indicating the location of DLA 400 in the network, historical anomalies in the network, or any other information that allow the user to assess the detected anomaly.

In general, machine learning results fall into one of four categories: true positives, true negatives, false positives, and false negatives. In the context of anomaly detection, true positives refer to detected anomalies that are indeed anomalies. Conversely, true negatives refer to model outputs that correctly identify normal conditions in the network (e.g., when the behavior of the network is indeed normal). False positives, meanwhile, refer to raised anomalies that are not truly anomalous or otherwise of relevance in the system. For example, a newly deployed application in the network may cause traffic pattern changes that could be deemed anomalous, but are otherwise representative of the new normal state of the network and, therefore, irrelevant. False negatives represent the opposite case in which the anomaly detector deems the network to be operating normally when, in fact, an anomalous condition exists. In particular, if the statistical model has adapted to repeated or continuous anomalies, it may begin producing false negatives since the anomalous conditions have polluted the training set of the model.

In FIG. 6C, UI process 512 of client device 504 may provide feedback 606 back to DLA 400, such as via SCA 502. In general, feedback 606 may indicate whether the detected anomaly is indeed relevant (e.g., a true positive) or, alternatively, irrelevant (e.g., a false positive, a true positive that the user does not believe to be relevant, etc.).

In FIG. 6D, in response to feedback 606, anomaly manager 506 of DLA 400 may control the training set of model 410 accordingly. For example, DLA 400 may determine that the triggered anomaly was a true positive based on feedback 606 and take measures to ensure that the corresponding set of sample data does not pollute the training set of model 410. Notably, in various embodiments, anomaly manager 506 may take any or all of the following actions:

If the anomaly is deemed relevant (e.g., a true positive) anomaly manager 506 may discard the corresponding set of samples without training the behavioral analytics model 410.

If the anomaly is deemed not relevant, anomaly manager 506 may train the behavioral analytics model 410 with the corresponding set of samples.

In other words, if DLA 400 determines that the detected anomaly was indeed relevant, DLA 400 may take measures to ensure that the set of sample data that triggered the anomaly is excluded from the training set for behavioral analytics model 410. Conversely, if DLA 400 determines that the detected anomaly is instead irrelevant based on feedback 606, it may take explicit measures to ensure that the set of sample data is used to train behavioral analytics model 410, thereby lowering the possibility of the network state triggering a subsequent anomaly.

In some embodiments, anomaly manager 506 may enable a local feedback timer when a given anomaly is raised or otherwise reported to SCA 502. If the feedback timer expires before DLA 400 receives feedback regarding a raised anomaly, anomaly manager 506 may proceed to train model 410 using the set of sample data that triggered the anomaly. Optionally, anomaly manager 506 may also store the set of sample data for an additional period of time, should DLA 400 receive feedback after expiration of the feedback timer. If, for example, DLA 400 receives feedback indicating that the anomaly is relevant (e.g., a true positive) after expiration of the feedback timer, anomaly manager 506 may remove or otherwise revert the behavioral analytics model 410 to exclude the set of sample data that triggered the anomaly from the training set for model 410.

Figure 7A:
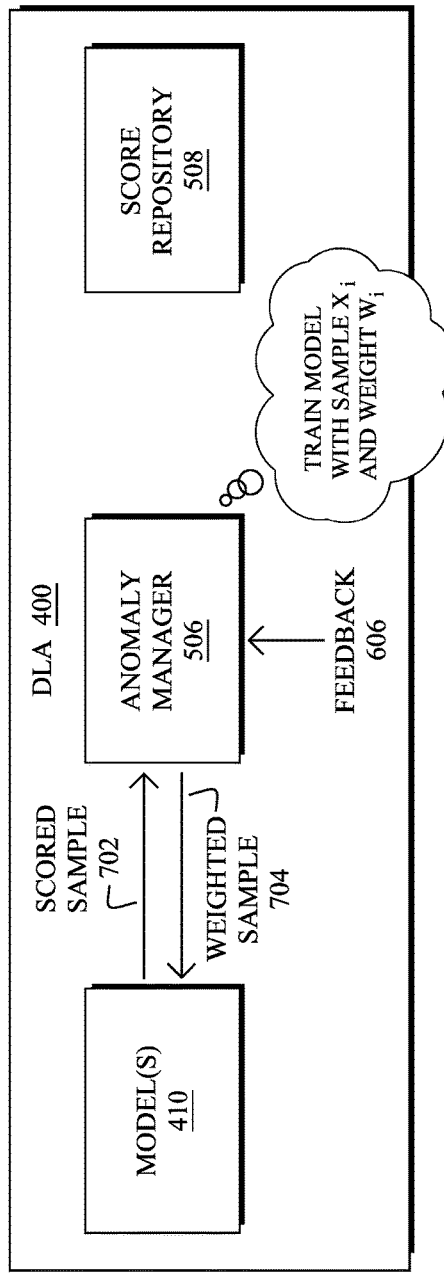
FIGS. 7A-7B illustrate examples of a DLA training an anomaly detection model.
Figure 7B:
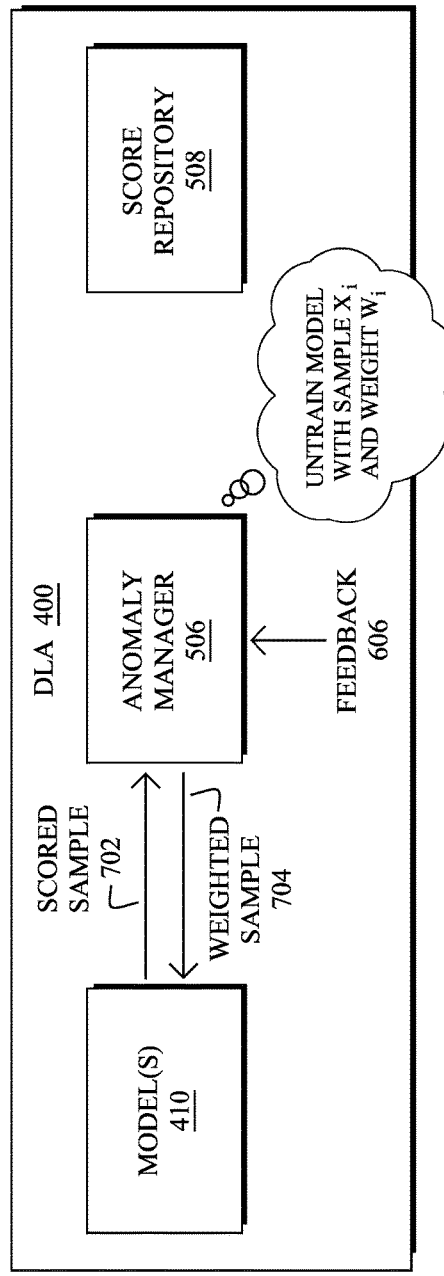

FIGS. 7A-7B illustrate examples of DLA 400 training an anomaly detection model 410, according to various embodiments. Depending on the configuration of anomaly manager 506, DLA 400 may take one of two approaches to training model(s) 410. As shown in FIG. 7A, anomaly manager 506 may receive scored sample data 702 from model(s) 410 and report anomalies as needed based on the results of the analysis. In turn, anomaly manager 506 may rely on feedback 606 to control whether sample data 702 is used as part of the training set to train model(s) 410. Notably, if anomaly manager 506 determines that the anomaly is a true positive based on feedback 606, it may exclude sample data 702 from the training set.

In FIG. 7B, anomaly manager 506 may also take the approach of first using a set of sample data to train model(s) 410 and later adjusting/reverting the model as needed. For example, if anomaly manager 506 does not receive feedback 606 before expiration of a feedback timer, anomaly manager 506 may use sample data 702 to train model(s) 410. If anomaly manager 506 then receives feedback 606 regarding the detected anomaly, anomaly manager 506 may "untrain" model(s) 410, to roll back the application of the sample data 702 to behavioral analytics model 410. In another embodiment, anomaly manager may immediately train model(s) 410 using any given sample $X_i$, but then "untrains" model(s) 410 based on feedback 606.

In one embodiment, the system may use a behavioral analytics model 410 that natively supports an untraining action. This includes most models that make use of an explicitly stored training set, such as many batch classification method or usual density estimators. In another embodiment, a behavioral analytics model 410 can be combined to an auxiliary model (e.g., another model in models 410) that acts as a proxy between the behavioral analytics model 410 and anomaly manager 506. The auxiliary model uses the statistical model to produce scores and to learn network behaviors, but may modulate some of the scores corresponding to cases that have been marked for unlearning. This auxiliary model may be realized either by explicitly storing all of the data points to be unlearned, but also through more compressed modeling (e.g., coding, locality sensitive hashing, or similar methods).

Another aspect of the techniques herein introduces a mechanism that adjusts the weight $W_i$ of a sample $X_i$. In particular, as shown in the configurations of both FIGS. 7A and 7B, anomaly manager 506 may apply a weighting to any set of sample data used to train model(s) 410. Of note is that most statistical models accept a weighted training set, and it is always possible to emulate this behavior by performing several iterations with the same sample. In this case, anomaly manager 506 may train model(s) 410 with a larger weight when the anomaly is deemed irrelevant, so as to ensure that such events are not raised anymore.

In a further aspect, the system may also apply a weight to user feedback 606, as well. Indeed, there may be situations in which a user considers an event as relevant while others may consider it irrelevant. Moreover, there may be situation where the degree of relevancy is itself weighted by the user. It is therefore important for the system to "adjust" the weight of the training/un-training step depending on the reliability of feedback 606. To compute the "weight" of feedback 606 (or, rather, its reliability), SCA 502 and/or DLA 400 may use a wide range of strategies. For example, SCA 502 may receive user feedback from a plurality of users or user devices, to determine an overall is relevancy weight sent to anomaly manager 506, as part of a voting strategy. In another example, SCA 502 may estimate the reliability of the user based on prior feedbacks. Regardless, anomaly manager 506 may use the weight indicated in feedback 606 to score sample data 702 when used to train model(s) 410.

Figure 8:
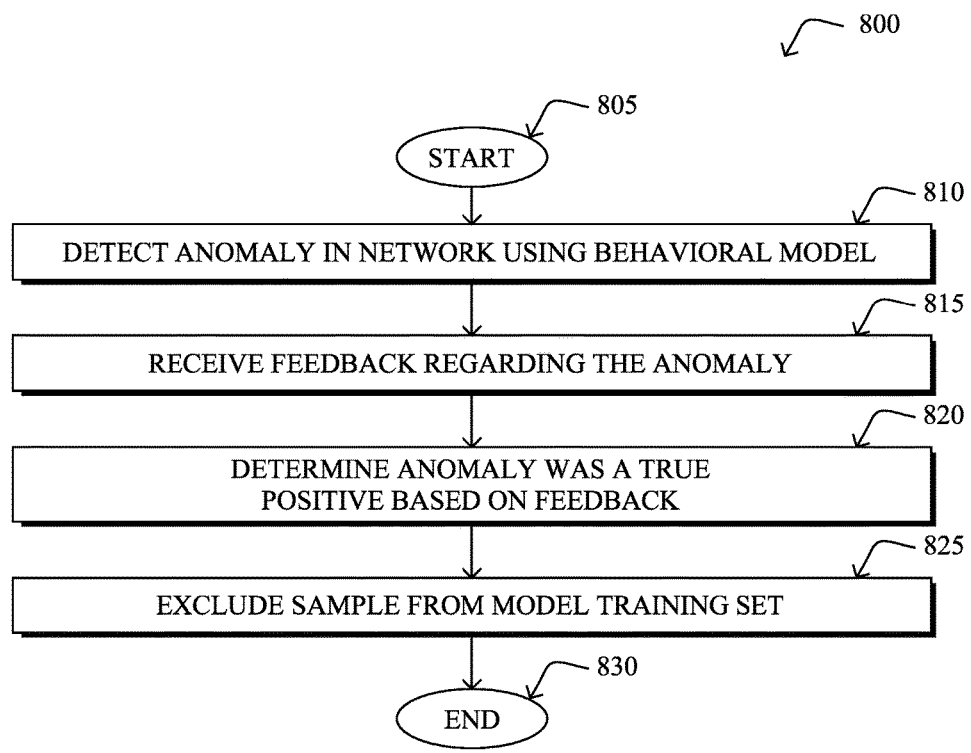
FIG. 8 illustrates an example simplified procedure for preventing an anomaly detector from learning an anomalous pattern.

FIG. 8 illustrates an example simplified procedure for preventing an anomaly detector from learning an anomalous pattern, in accordance with the embodiments herein. Generally, procedure 800 may be performed by a specialized device in a network, such as an edge router, a switch, or the like. Procedure 800 starts at step 805 and continues on to step 810 where, as described in greater detail above, the device may detect an anomaly in the network by analyzing a set of sample data regarding the network using a behavioral analytics model, such as a statistical model. Such a model may, for example, determine a probability of the set of sample data being observed in the network, given a training set of prior samples. Example sample data may include, but are not limited to, data regarding the applications or protocols associated with network traffic, the endpoint addresses and/or ports associated with the traffic flows, metrics regarding the flows (e.g., packet sizes, durations, etc.), combinations thereof, or any other information regarding the state of the network.

At step 815, as detailed above, the device may receive feedback regarding the detected anomaly. In some embodiments, the device may receive the feedback via one or more user interfaces. Generally, the feedback may indicate whether the detected anomaly is relevant (e.g., the anomaly is indeed a true positive) or, alternatively, irrelevant. In some cases, the relevancy of the anomaly may be rated in a binary manner, such as whether the anomaly is or is not relevant. In other cases, the relevancy may be rated on a scale. For example, some anomalies may be more irrelevant than others to the user or a group of users (e.g., based on a voting mechanism among users, etc.).

At step 820, the device may determine that the detected anomaly was a true positive based on the received feedback, as described in greater detail above. For example, the device may evaluate the relevancy indicated in the feedback, to determine whether the detected anomaly was indeed anomalous and relevant in the context of monitoring the operation of the network.

At step 825, as detailed above, the device may exclude the set of sample data from a training set for the behavioral analytics model. In particular, in response to determining that the anomaly was a true positive, the device may take steps to ensure that the set of sample data that triggered the anomaly is not used to train the model. Doing so protects the model from "learning" anomalous behaviors over time, thereby reducing the ability of the model to detect anomalous/malicious conditions in the network. In some embodiments, the device may simply hold off on training the model until the feedback is received in step 815, to ensure that the model is not polluted with the set of sample data. In further embodiments, the device may instead train the model using the set of sample data, but later revert the model to exclude the sample data, if the feedback indicates that the anomaly is a true positive. Procedure 800 then ends at step 830.

It should be noted that while certain steps within procedure 800 may be optional as described above, the steps shown in FIG. 8 are merely examples for illustration, and certain other steps may be included or excluded as desired. Further, while a particular order of the steps is shown, this ordering is merely illustrative, and any suitable arrangement of the steps may be utilized without departing from the scope of the embodiments herein.

The techniques described herein, therefore, introduce mechanisms that prevent anomaly detection models from being biased by prior occurrences of attacks, malware, intrusions, or other anomalies. In some aspects, the mechanisms may delay and/or revert the training of the underlying model with samples from a confirmed anomaly.

While there have been shown and described illustrative embodiments that provide for controlling the training of an anomaly detector, it is to be understood that various other adaptations and modifications may be made within the spirit and scope of the embodiments herein. For example, while certain embodiments are described herein with respect to using certain models for purposes of anomaly detection, the models are not limited as such and may be used for other functions, in other embodiments. In addition, while certain protocols are shown, such as BGP, other suitable protocols may be used, accordingly.

The foregoing description has been directed to specific embodiments. It will be apparent, however, that other variations and modifications may be made to the described embodiments, with the attainment of some or all of their advantages. For instance, it is expressly contemplated that the components and/or elements described herein can be implemented as software being stored on a tangible (non-transitory) computer-readable medium (e.g., disks/CDs/RAM/EEPROM/etc.) having program instructions executing on a computer, hardware, firmware, or a combination thereof. Accordingly this description is to be taken only by way of example and not to otherwise limit the scope of the embodiments herein. Therefore, it is the object of the appended claims to cover all such variations and modifications as come within the true spirit and scope of the embodiments herein.

What is claimed is:

1. A method comprising:
   detecting, by a device in a network, an anomaly in the network by analyzing a set of sample data regarding one or more conditions of the network using a behavioral analytics model;
   receiving, at the device, feedback regarding the detected anomaly;
   determining, by the device, that the anomaly was a true positive based on the received feedback; and
   excluding, by the device, the set of sample data from a training set for the behavioral analytics model, in response to determining that the anomaly was a true positive by:
     training, by the device, the behavioral analytics model using the set of sample data as part of the training set, wherein training includes:
       determining, by the device, that expiration of a feedback timer has occurred based on the device not receiving the feedback regarding the detected anomaly within a feedback time period, wherein the device trains the behavioral analytics model using the set of sample data as part of the training set in response to the expiration of the feedback time, and
       storing, by the device, the set of sample data for a retention period of time to revert the behavioral analytics model after training the behavioral analytics model using the set of sample data, in case the feedback regarding the detected anomaly is received after expiration of the feedback timer, and
     reverting, by the device, the behavioral analytics model to exclude the set of sample data from the training set, in response to determining that the anomaly was a true positive.

2. The method as in claim 1, wherein the device is an edge router.

3. The method as in claim 1, further comprising:
   providing, by the device, information regarding the detected anomaly to a user interface, wherein the feedback regarding the detected anomaly is received via the user interface.

4. The method as in claim 1, further comprising:
   determining, by the device, that a second anomaly detected by the behavioral analytics model is irrelevant; and
   training, by the device, the behavioral analytics model using a second set of sample data that caused the behavioral analytics model to detect the second anomaly, wherein a weight of the second set of sample data is increased in the training set for the behavioral analytics model based on the determination that the second anomaly is irrelevant.

5. The method as in claim 4, further comprising:
training, by the device, the behavioral analytics model using the second set of sample data; and
retraining, by the device, the behavioral analytics model using the second set of sample data with the increased weight, in response to determining that the second anomaly is irrelevant.

6. The method as in claim 4, wherein determining that the second anomaly detected by the behavioral analytics model is irrelevant comprises:
receiving, at the device, feedback from a user interface regarding the second anomaly that indicates that the second anomaly is irrelevant, wherein the weight of the second set of sample data is based on the received feedback regarding the second anomaly.

7. An apparatus, comprising:
one or more network interfaces to communicate with a network;
a processor coupled to the network interfaces and configured to execute one or more processes; and
a memory configured to store a process executable by the processor, the process when executed operable to:
detect an anomaly in the network by analyzing a set of sample data regarding one or more conditions of the network using a behavioral analytics model;
receive feedback regarding the detected anomaly;
determine that the anomaly was a true positive based on the received feedback; and
exclude the set of sample data from a training set for the behavioral analytics model, in response to determining that the anomaly was a true positive by:
training, by the device, the behavioral analytics model using the set of sample data as part of the training set, wherein training includes:
determining, by the device, that expiration of a feedback timer has occurred based on the device not receiving the feedback regarding the detected anomaly within a feedback time period, wherein the device trains the behavioral analytics model using the set of sample data as part of the training set in response to the expiration of the feedback time, and
storing, by the device, the set of sample data for a retention period of time to revert the behavioral analytics model after training the behavioral analytics model using the set of sample data, in case the feedback regarding the detected anomaly is received after expiration of the feedback timer, and
reverting, by the device, the behavioral analytics model to exclude the set of sample data from the training set, in response to determining that the anomaly was a true positive.

8. The apparatus as in claim 7, wherein the apparatus is an edge router.

9. The apparatus as in claim 7, wherein the process when executed is further operable to:
provide information regarding the detected anomaly to a user interface, wherein the feedback regarding the detected anomaly is received via the user interface.

10. The apparatus as in claim 7, wherein the process when executed is further operable to:
determine that a second anomaly detected by the behavioral analytics model is irrelevant; and
train the behavioral analytics model using a second set of sample data that caused the behavioral analytics model to detect the second anomaly, wherein a weight of the second set of sample data is increased in the training set for the behavioral analytics model based on the determination that the second anomaly is irrelevant.

11. The apparatus as in claim 10, wherein the process when executed is further operable to:
train the behavioral analytics model using the second set of sample data; and
retrain the behavioral analytics model using the second set of sample data with the increased weight, in response to determining that the second anomaly is irrelevant.

12. The apparatus as in claim 11, wherein the apparatus determines that the second anomaly detected by the behavioral analytics model is irrelevant by:
receiving feedback from a user interface regarding the second anomaly that indicates that the second anomaly is irrelevant, wherein the weight of the second set of sample data is based on the received feedback regarding the second anomaly.

13. A tangible, non-transitory, computer-readable medium storing program instructions that cause a device in a network to execute a process comprising:
detecting an anomaly in the network by analyzing a set of sample data regarding one or more conditions of the network using a behavioral analytics model;
receiving feedback regarding the detected anomaly;
determining that the anomaly was a true positive based on the received feedback; and
excluding the set of sample data from a training set for the behavioral analytics model, in response to determining that the anomaly was a true positive by:
training, by the device, the behavioral analytics model using the set of sample data as part of the training set, wherein training includes:
determining, by the device, that expiration of a feedback timer has occurred based on the device not receiving the feedback regarding the detected anomaly within a feedback time period, wherein the device trains the behavioral analytics model using the set of sample data as part of the training set in response to the expiration of the feedback time, and
storing, by the device, the set of sample data for a retention period of time to revert the behavioral analytics model after training the behavioral analytics model using the set of sample data, in case the feedback regarding the detected anomaly is received after expiration of a feedback timer, and
reverting, by the device, the behavioral analytics model to exclude the set of sample data from the training set, in response to determining that the anomaly was a true positive.

14. The computer-readable medium as in claim 13, wherein the feedback regarding the detected anomaly comprises votes received from a plurality of user interfaces as to whether the detected anomaly is relevant.

* * * * *

UNITED STATES PATENT AND TRADEMARK OFFICE
CERTIFICATE OF CORRECTION

PATENT NO. : 10,220,167 B2
APPLICATION NO. : 15/180675
DATED : March 5, 2019
INVENTOR(S) : Gregory Mermoud et al.

Page 1 of 1

It is certified that error appears in the above-identified patent and that said Letters Patent is hereby corrected as shown below:

In the Specification

In Column 6, Line 54, please amend as shown:
behaviors such as malware, viruses, rootkits, etc. may In Column 16, Line 46, please amend as shown:
devices, to determine an overall relevancy weight sent to Signed and Sealed this
Seventh Day of January, 2020

Andrei Iancu
*Director of the United States Patent and Trademark Office*